Aug. 2, 1966 J. W. PATTERSON Plant Pat. 2,661
ROSE
Filed April 12, 1965
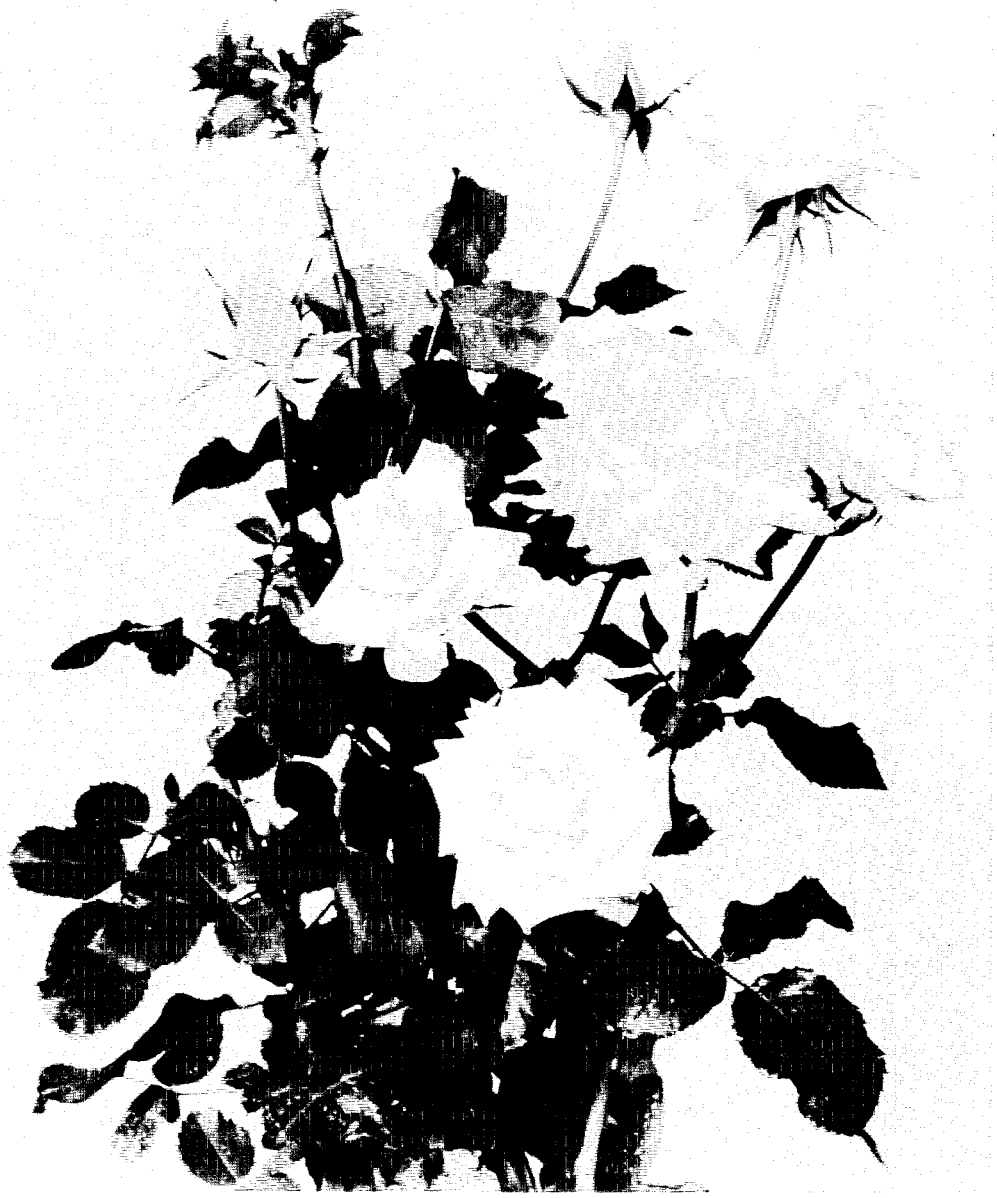
John W. Patterson
INVENTOR
J. Vincent Martin
Joe E. Edwards
A. H. Evans
ATTORNEYS

United States Patent Office

Plant Pat. 2,661
Patented August 2, 1966

2,661
ROSE

John W. Patterson, 6518 Kernel, Houston, Tex. 77017

Filed Apr. 12, 1965, Ser. No. 447,590
1 Claim. (Cl. Plt.—22)

The present invention relates to a new and distinct variety of rose plant of the floribunda class, which was originated by me by crossing the variety "Carrousel" (Plant Patent No. 1,066) with an unnamed multi-color seedling variety.

The primary objective in making this cross was to produce a new variety of rose plant which combines the most desirable characteristics of the two parent varieties. The object was achieved, as seen by the fact that my new variety is characterized by an unusual color progression of its blooms which at first are yellow, with markings of red, but which change later to red with cream underlay in the older blooms. In addition to this unique color progression, my new variety is characterized by its leathery foliage as inherited from the parent "Carrousel," by its strong fragrance inherited from both parents, long lasting qualities from "Carrousel" and by the many-flowered cluster habit of its blooms at times as inherited from both parent varieties.

In comparison with its seed parent, "Carrousel"; my new variety is definitely distinguished from its parent by the fact that the blooms of the new variety are multi-colored, whereas those of "Carrousel" are red, the new variety has 30 to 35 petals whereas "Carrousel" only has about 20 petals; and the petal substance of the blooms of my new variety is greater than that of its seed parent.

As compared with its pollen parent (an unnamed and unpatented seedling) my new variety is distinct therefrom as evidenced by the fact that the blooms of the new variety are larger in size than those of this parent, being from 2½" to 3" in diameter, whereas the blooms of its parent are never over 2 inches in diameter. My new variety has an abundance of leathery foliage, whereas the foliage of its pollen parent is less abundant.

Asexual reproduction of my new variety by budding as performed at Houston, Texas, and Wills Point, Texas, shows that the foregoing characteristics and distinctions of my new variety come true to form and are established and transmitted through succeeding propagations.

The accompanying drawing shows typical specimens of the blooms and foliage of my new variety in different stages of development, as depicted in color as nearly true as it is reasonably possible to make the same in a color illustration of this character.

The following is a detailed description of my new variety, with color terminology in accordance with the Horticultural Colour Chart of the Royal Horticultural Society:

Type: Bush; outdoor; seedling for garden decoration.
Class: Floribunda.
Breeding: Seedling.
*Seed parent.*—"Carrousel."
*Pollen parent.*—Unnamed multicolor seedling.
Propagation: Holds its distinguishing characteristics through succeeding propagations by budding.

*Flower*

Locality where grown and observed: Houston, Texas, also Wills Point, Texas.
Flowers borne: Usually several to stem, sometimes only one to stem.
Quantity of bloom: Free to abundant, outdoors.
Continuity: Continuous during growing season.

Fragrance: Moderate. Nature—spicy.
Bud:
*Peduncle.*—Average length, average caliper; moderately smooth; few soft prickles.
*Color.*—Scheeles Green, Plate 860/3, page 175.
*Before calyx breaks.*—Size—medium. Form—medium length; ovoid; with foliaceous appendages; with very few cilia on the surface of bud.
*As calyx breaks.*—Color—Aureolin, Plate 3/3, page 3, heavily overlaid with Delft Rose, Plate 020/1, page 108, and Mars Orange, Plate 013/2, page 104.
*Sepals.*—Inner surface with fine woolly tomentum; color—inside near Spinach Green, Plate 0960/3, page 187. Outside—Scheeles Green, Plate 860/3, page 175, overlaid with Erythrite Red, Plate 0027/2, page 190.
*As first petal opens.* — Size — small to average. Form—ovid. Color: outside—Delft Rose, Plate 020/1, page 108, sometimes Mars Orange, Plate 013/2, page 104, mingled with Aureolin, Plate 3/2, page 3. Base of petal (about ⅛ size) Sulphur Yellow, Plate 1/2, page 1. Inside—Geranium Lake, Plate 20, page 20, overlaid somewhat with Jasper Red, Plate 018, page 107, base (about ⅛ size of petal) Aureolin, Plate 3/2, page 3.
*Opening.*—Opens up well; is not retarded by hot, cold, dry or wet weather.
Bloom:
*Size when fully open.*—2½ inches to 3 inches.
*Petalage.*—Very double: about 30 petals, plus 6 to 8 petaloids; regularly arranged.
*Form.*—High-centered at first; becoming flat to open later. Sometimes petals become reflexed for approximately ¼ of petal length.
Petals:
*Texture.*—Thick; with both inside and outside slightly satiny.
*Shape.*—Broadly obovate. Intermediate—obovate. Inside—obovate.

This description of a newly opened flower was made from a rose grown outdoors in the month of October, at Houston, Texas.

*Color.*—Outside petal: outside surface—Aureolin, Plate 3/3, page 3, overlaid with Claret Rose, Plate 021/1, page 109, small area of base at attachment Lemon Yellow, Plate 4/2, page 4. Inside surface—upper ¼ petal Delft Rose, Plate 020/1, page 108; ¾ petal lower between Aureolin, Plate 3/3, page 3 and Lemon Yellow, Plate 4/3, page 4; remainder of petal at base Lemon Yellow, Plate 4/1, page 4. Intermediate petal: outside surface—Buttercup Yellow, Plate 5/2, page 5. Upper portion of petal slightly mingled with Brick Red, Plate 016/3, page 106, overlay. Inside surface—near Saffron Yellow, Plate 7/3, page 7, very slightly overlaid with Delft Rose, Plate 020/3, page 108. Base of petal near attachment Aureolin, Plate 3/1, page 3. Inner Petal: outside surface—Aureolin, Plate 3/2, page 3, only very slightly shaded with Jasper Red, Plate 018/3, page 107. Base of petal Aureolin, Plate 3/2, page 3. Inside surface—Aureolin, Plate 3/2, page 3, very slightly overlaid with Jasper Red, Plate 018/3, page 107. Base of petal Aureolin, Plate 3/1, page 3.

This description was made from a rose that was open for 3 days outdoors in the month of October, at Houston, Texas.

*Color.*—Outside petal: outside surface—Aureolin,

Plate 3/3, page 3, overlaid with Cardinal Red, Plate 822/3, page 168, on upper portion of petal. Base of petal Lemon Yellow, Plate 4/3, page 4. Inside surface—Aureolin, Plate 3/3, page 3, heavily overlaid with Blood Red, Plate 820/1, page 166, on upper ½ petal. Lower ½ petal Lemon Yellow, Plate 4/3, page 4, with base Lemon Yellow, Plate 4/2, page 4. Inside petal: outside surface—Lemon Yellow, Plate 4/3, page 4, overlaid with Delft Rose, Plate 020/2, page 108, ¾ of petal. Base of petal Lemon Yellow, Plate 4/2, page 4. Inside surface—Lemon Yellow, Plate 4/3, page 4, heavily overlaid with Blood Red, Plate 82/0, page 166, tip of base of petal Aureolin, Plate 3/2, page 3.

*General color effect.*—Newly opened flower—Geranium Lake, Plate 20/1, page 20, with outer tips of petals darker showing Cardinal Red, Plate 822, page 168, nearer base of petals near attachment Aureolin, Plate 3/3, page 3, to Tangerine Orange, Plate 9/2, page 9. 3-days open flower—Aureolin, Plate 3/3, page 3, overlaid with Burnt Orange, Plate 014/1, and Blood Red, Plate 820/1, page 166.

*Behavior.*—Drop off cleanly, color heightened in Autumn.

*Flower longevity.*—On bush in garden—5 to 6 days in October. Cut roses grown outdoors and kept at living-room temperatures—5 to 6 days in October.

*Reproductive organs*

Stamens: Average number, arranged regularly about pistils; a few mixed with petaloids.

Filaments: Short length; most with anthers. Color—near Sulphur Yellow, Plate 1/2, page 1.

Anthers: Medium size; all open approximately at once. Color—near Indian Yellow, Plate 6/2, page 6.

Pollen: Moderate. Color—near Indian Yellow, Plate 6/2, page 6.

Pistils: Average number.

Styles: Moderate, average length, thin caliper, bunched. Color—Canary Yellow, Plate 2/3, page 2, to Canary Yellow 2, page 2.

Stigma: Color—Yellow Ochre 07/2, page 101.

Hips: None.

*Plant*

Foliage:

*Leaves.*—Compound of usually 5 to 7 leaflets abundant; medium in size, leathery.

*Leaflets.*—Shape—ovoid. Base—round. Margin—serrate.

*Color.*—Mature: Upper surface—Spinach Green, Plate 0960, page 187. Under surface—Spinach Green, Plate 0960/3, page 187, slightly overlaid with Pansy Purple, Plate 928, page 177. Young: Upper surface—Willow Green, Plate 000862, page 199, heavily overlaid with Maroon, Plate 1030, page 185. Under surface—Pansy Purple, Plate 928, page 177.

*Rachis (the supporting stem of the compound leaf).*—average size. Upper side—grooved and hairy. Under side—very prickly.

*Stipules.*—Short to medium, medium width, with medium length points turning out at an angle of more than 45°.

*Disease resistance.*—Very resistant to mildew and blackspot, compared with other varieties grown under comparable cultural conditions at Houston, Texas.

Growth:

*Habit.*—Moderate—compact and bushy.

*Growth.*—Free, moderate.

*Canes.*—Medium diameter.

*Main stems.*—Color—Spinach Green, Plate 0960/1, page 187. Large prickles—several to many, slightly hooked downward; with flat base. Color—Greyish brown (no color in chart listed).

*Branches.*—Color—Scheeles Green, Plate 860, page 175. Large prickles, several to many, slightly hooked downward; color—Fern Green, Plate 0862/1, page 186. Small prickles—several; color—Pod Green, Plate 061, page 120.

*New shoots.*—Color—Scheeles Green, Plate 860/3, page 175, slightly overlaid with Purple Madder, Plate 1028/3, page 181. Large prickles—average number, hooked downward; color—near Purple Madder, Plate 1028/3, page 181. Small prickles—several; color—near Erythrite Red, Plate 0027/1, page 190.

I claim:

A new and distinct variety of rose plant of the floribunda class, substantially as herein shown and described, characterized particularly as to novelty by the combination of a distinctive color progression of its blooms from yellow, with some markings of red at first, to almost red with cream underlay as the bloom ages, by the moderate fragrance and good petal substance of its blooms, with attendant long-lasting quality thereof, by the very double petalage and the many-flowered cluster habit of its blooms, and by its abundant and leathery foliage.

No references cited.

ABRAHAM G. STONE, *Primary Examiner.*

R. E. BAGWILL, *Assistant Examiner.*